United States Patent
Lee

(10) Patent No.: US 10,507,314 B2
(45) Date of Patent: Dec. 17, 2019

(54) SKIN RESURFACING DEVICE, CONTROLLING APPARATUS AND CONTROLLING METHOD FOR SKIN RESURFACING DEVICE

(71) Applicant: Seung-Ho Lee, Gyeonggi-do (KR)

(72) Inventor: Seung-Ho Lee, Gyeonggi-do (KR)

( * ) Notice: Subject to any disclaimer, the term of this patent is extended or adjusted under 35 U.S.C. 154(b) by 507 days.

(21) Appl. No.: 15/272,400

(22) Filed: Sep. 21, 2016

(65) Prior Publication Data

US 2017/0087347 A1    Mar. 30, 2017

(30) Foreign Application Priority Data

Sep. 24, 2015   (KR) .................. 10-2015-0135177

(51) Int. Cl.
| | | |
|---|---|---|
| *A61M 37/00* | (2006.01) | |
| *A61B 17/50* | (2006.01) | |
| *A61B 17/54* | (2006.01) | |
| *A61B 17/00* | (2006.01) | |
| *A61B 17/20* | (2006.01) | |

(52) U.S. Cl.
CPC .......... *A61M 37/0076* (2013.01); *A61B 17/50* (2013.01); *A61B 17/54* (2013.01); *A61B 17/205* (2013.01); *A61B 2017/00115* (2013.01); *A61B 2017/00747* (2013.01); *A61B 2017/00761* (2013.01)

(58) Field of Classification Search
CPC .......... A61B 17/50; A61B 2017/00132; A61B 2017/00747; A61B 2017/00761; A61B 2017/00765; A61B 2017/00769; A61M 37/0076
See application file for complete search history.

(56) References Cited

U.S. PATENT DOCUMENTS

2001/0034519 A1* 10/2001  Goble ................ A61B 18/042
                                                        606/41
2008/0300615 A1* 12/2008  Colton .............. A61M 37/0076
                                                        606/186

* cited by examiner

*Primary Examiner* — Jocelin C Tanner
(74) *Attorney, Agent, or Firm* — TIPS Group

(57) ABSTRACT

The present invention provides a controlling apparatus for a skin resurfacing device performing a surgical procedure on a human skin with a surgical needle, including: a controller 20; a voltage regulator 50 configured to regulate a voltage supplied to the skin resurfacing device from a power supply 10 according to a control of the controller; and a starting switch 80 configured to turn on/off a supply of power between the voltage regulator and the skin resurfacing device, in which the controller controls the voltage regulator so as to output a preset jump start voltage to the skin resurfacing device every time the starting switch is turned on, if a jump start function that is a function of starting the skin resurfacing device is set by a starting voltage when an operating voltage of the skin resurfacing device is lower than the starting voltage of the skin resurfacing device at the time of the surgical procedure.

4 Claims, 3 Drawing Sheets

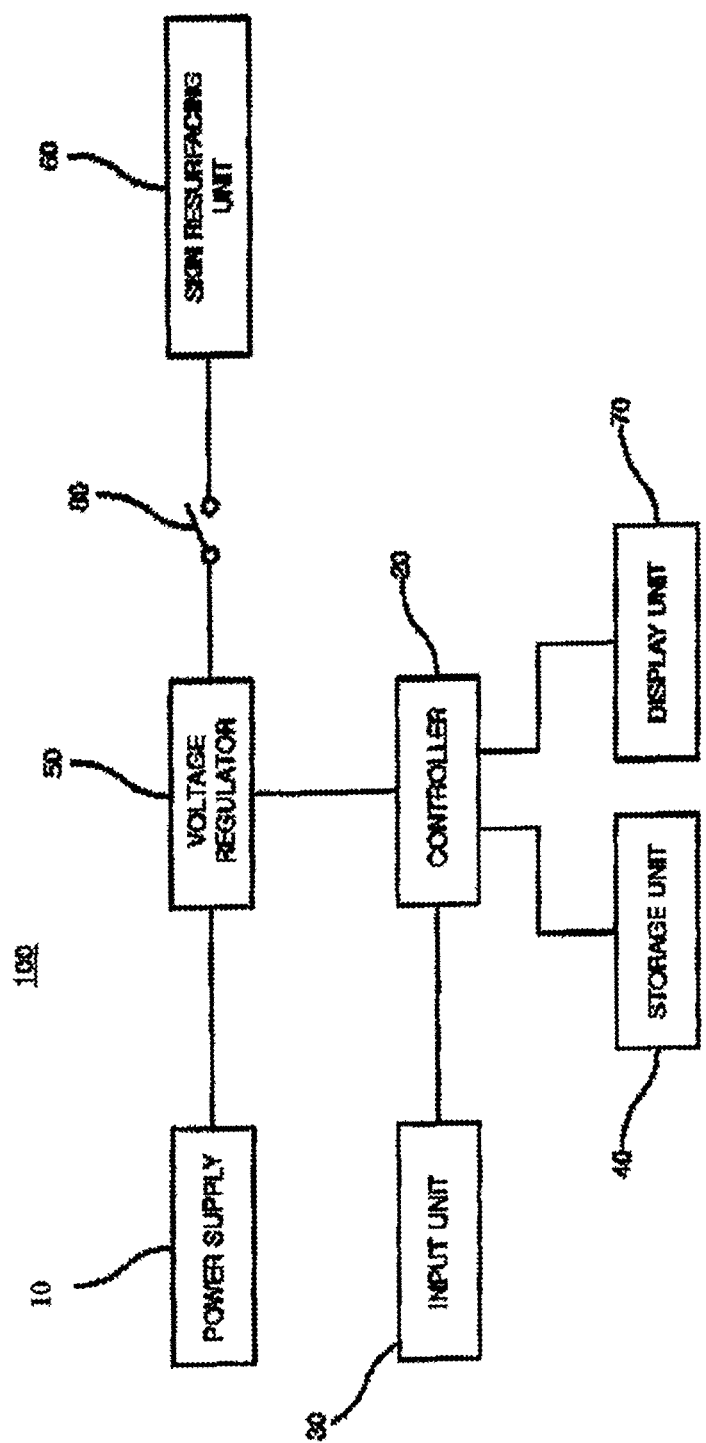
[FIG. 1]

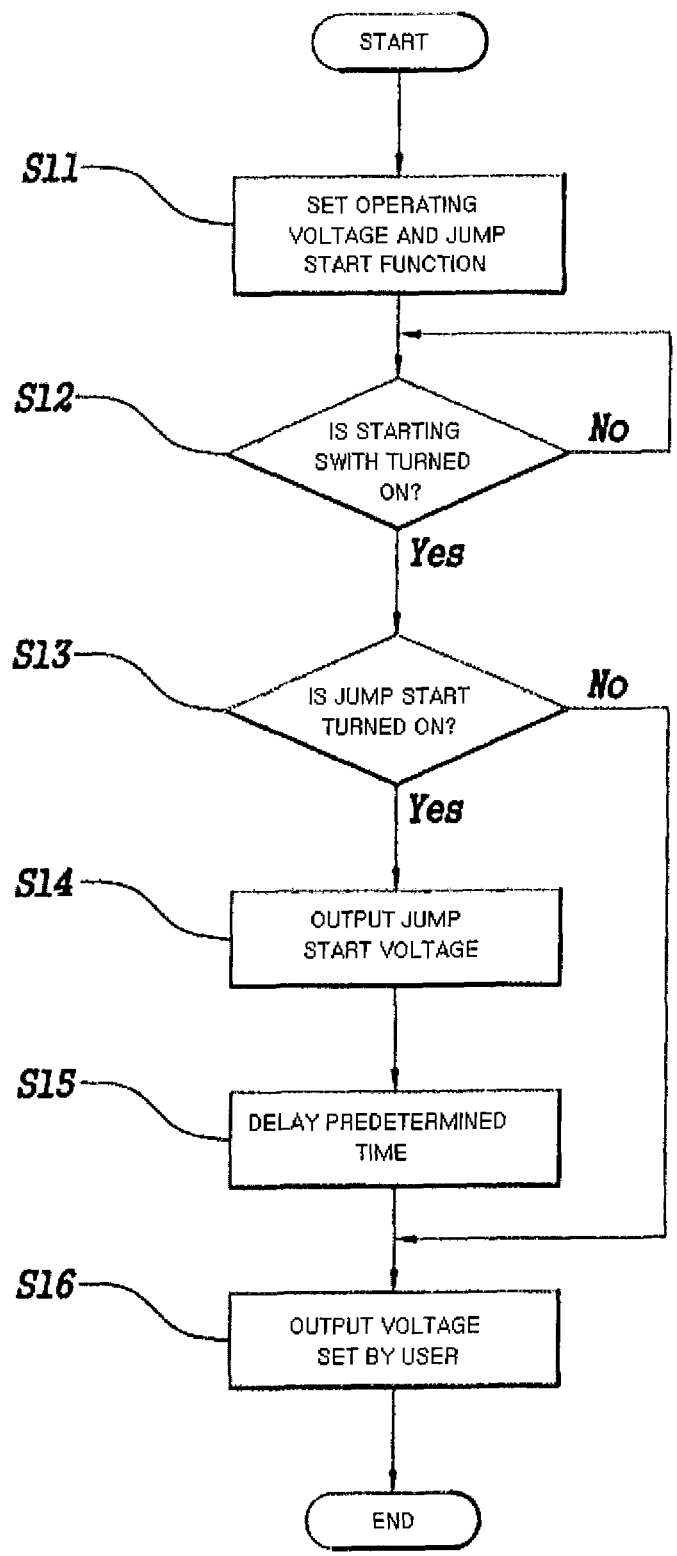
[FIG. 2]

[FIG. 3]
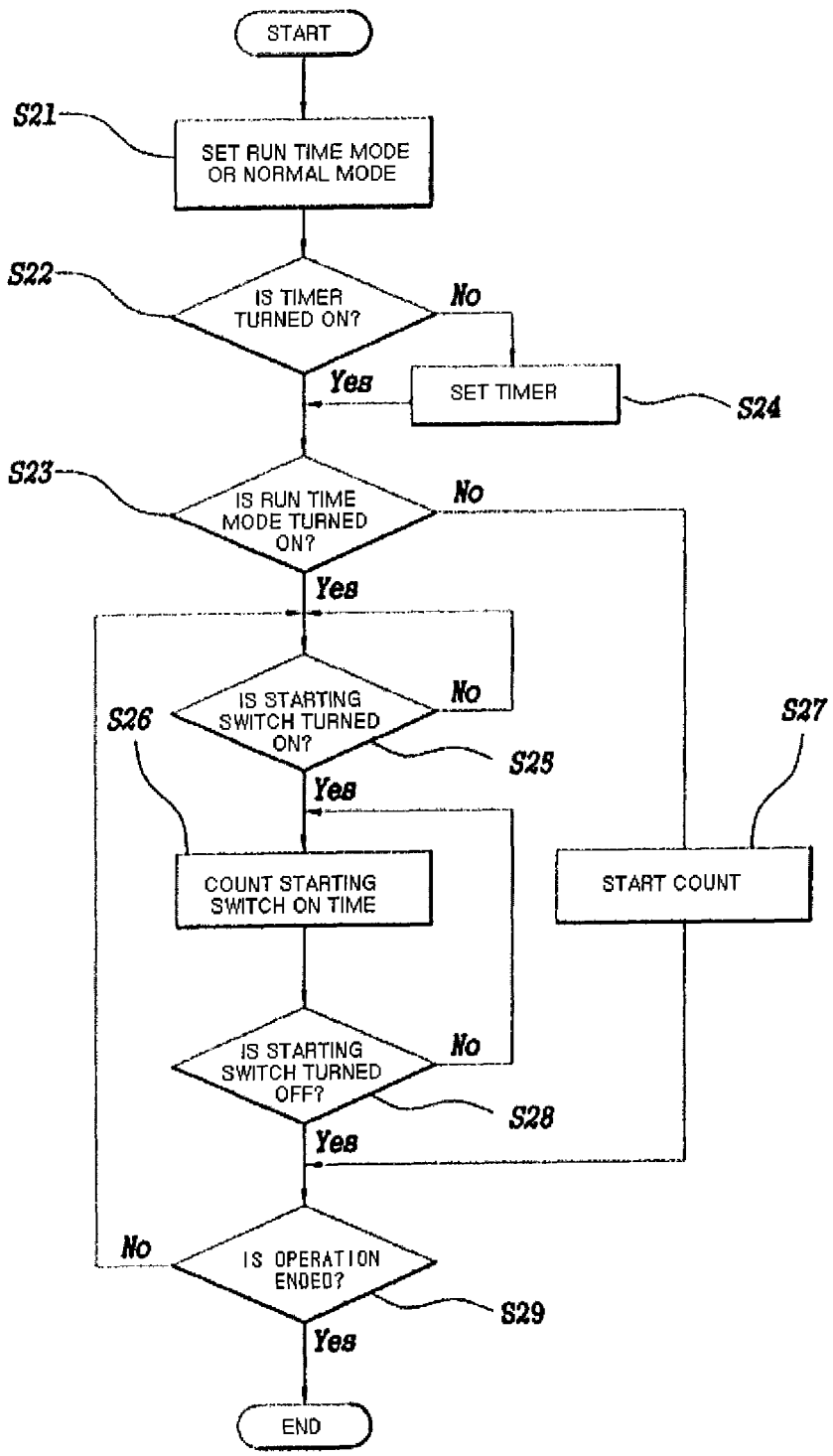

SKIN RESURFACING DEVICE, CONTROLLING APPARATUS AND CONTROLLING METHOD FOR SKIN RESURFACING DEVICE

RELATED APPLICATIONS

This application claims priority to Korean Patent Application No. 10-2015-0135177, filed on Sep. 24, 2015, in the Korean Intellectual Property Office, the entire disclosure of which is incorporated herein by reference.

BACKGROUND OF THE INVENTION

1. Field of the Invention

The present invention relates to a skin resurfacing device capable of treating and tattooing a human skin with a surgical needle and a controlling apparatus and a controlling method for skin resurfacing device.

2. Description of the Related Art

Skin resurfacing has been made by various methods according to purposes such as cosmetic treatment, treatment, and tattoo. For example, the skin resurfacing for treatment purpose to remove wrinkles, pimples, or the like makes many micro holes on a human skin with a needle to inject a treatment drug into the micro holes while granulating due to autogenic power of a skin tissue damaged during the process, thereby increasing a resurfacing effect.

Further, for tattooing, ink for a tattoo flows into a skin along a needle while the skin is pricked with the needle to carve pictures, letters, patterns, or the like into a skin.

As a prior art relating to such the skin resurfacing device, there is a technique described in Korean Patent Laid-Open Publication No. 2014-0108071 (published on Sep. 5, 2014).

The skin resurfacing device described in the above patent includes: a plurality of magnet sensing pieces radially coupled with an outer circumferential surface of a rotating body that is coupled with a driving shaft of a motor to rotate along with the driving shaft; and a sensing sensor configured to sense revolutions per minute (RPM) of the plurality of magnet sensing pieces, in which when the rotating body rotates by the rotation of the driving shaft, the plurality of magnet sensing pieces rotate together, and the rotation of the magnet sensing piece is sensed by the sensing sensor, such that a controlling apparatus performs a control to correct the irregular RPM of the motor to a regular RPM, or increase or decrease the RPM.

However, the above patent only describes that the rotation of the magnet sensing pieces is sensed by the sensing sensor, and thus the controlling apparatus performs the control to correct the irregular RPM of the motor to the regular RPM or increase or decrease the RPM. As a result, the above patent does not describe how the controlling apparatus corrects the irregular RPM of the motor to the regular RPM, or increases or decreases the RPM.

Meanwhile, there is a need to control an operating speed of the skin resurfacing device within various ranges such as a high speed or a low speed depending on a surgical procedure condition. For this purpose, a method for increasing or decreasing the rotation of the motor by controlling a power supply voltage applied to the skin resurfacing device may be used.

However, for example, when the skin resurfacing device is a device that uses a torque of a DC motor as a driving source, a minimum driving voltage that is a voltage for first rotating the DC motor in a state in which the DC motor stops and an operating voltage in a state in which the DC motor starts once may be different from each other, and the minimum driving voltage is generally higher than the operating voltage, which goes for even a case in which the skin resurfacing device uses other schemes other than the DC motor as the driving source.

For example, a minimum driving voltage of any skin resurfacing device is 12V, but after the skin resurfacing device is driven once, the skin resurfacing device may be driven within a range between 6 V and 12 V. When an operator intends to perform a surgical procedure while operating the skin resurfacing device at a voltage of 6 V, a user needs to perform an operation of setting the voltage of the skin resurfacing device to be 12 V to drive the skin resurfacing device once, and then to lowering the voltage to 6 V again after the skin resurfacing device is normally driven. In the skin resurfacing to frequently drive and stop the skin resurfacing device, the operation cannot but be a very cumbersome operation. However, a prior art for solving the above problems does not exist yet.

Further, for example, like a tattoo, in the surgical procedure using the skin resurfacing device, there may be cases in which surgical procedure cost is collected depending on a surgical procedure time. As a scheme of counting the resurfacing time, there may be a scheme of counting a total time from beginning to end of the surgical procedure or a scheme of counting only time when the skin resurfacing device is actually driven. However, the existing technology of selectively counting the two schemes does not exist yet.

SUMMARY OF THE INVENTION

An object of the present invention is to provide a skin resurfacing device, and a controlling apparatus and a controlling method for a skin resurfacing device, in which if a jump start function is performed in a state in which the user sets a use voltage in a normal use state of the skin resurfacing device, the controlling apparatus for the skin resurfacing device automatically supplies a voltage corresponding to an initial driving voltage to drive the skin resurfacing device and once the skin resurfacing device is driven, the user operates the skin resurfacing device at the set use voltage.

Another object of the present invention is to provide a skin resurfacing device capable of selectively setting, by a user, a scheme of counting a total time from beginning to end of a surgical procedure using the skin resurfacing device or a scheme of counting only time when the skin resurfacing device is actually driven, and a controlling apparatus and a controlling method for a skin resurfacing device.

In order to accomplish the above-described objects, according to an aspect of the present invention, there is provided a controlling apparatus for a skin resurfacing device performing a surgical procedure on a human skin with a surgical needle, including: a controller; a voltage regulator configured to regulate a voltage supplied to the skin resurfacing device from a power supply according to a control of the controller; and a starting switch configured to turn on/off a supply of power between the voltage regulator and the skin resurfacing device, wherein the controller controls the voltage regulator so as to output a preset jump start voltage to the skin resurfacing device every time the starting switch is turned on, if a jump start function that is a function of starting the skin resurfacing device is set by a starting voltage when an operating voltage of the skin resurfacing device is lower than the starting voltage of the skin resurfacing device at the time of the surgical procedure.

According to another aspect of the present invention, there is provided a skin resurfacing device performing a surgical procedure on a human skin with a surgical needle, including: a skin resurfacing unit which includes at least the needle and performs treatment or tattoo; a controller; a voltage regulator configured to regulate a voltage supplied to the skin resurfacing unit from a power supply according to a control of the controller; and a starting switch configured to turn on/off a supply of power between the voltage regulator and the skin resurfacing unit, wherein the controller controls the voltage regulator so as to output a preset jump start voltage to the skin resurfacing device every time the starting switch is turned on, if a jump start function that is a function of starting the skin resurfacing device is set by a starting voltage when an operating voltage of the skin resurfacing device is lower than the starting voltage of the skin resurfacing unit at the time of the surgical procedure.

According to another aspect of the present invention, there is provided a controlling method for a skin resurfacing device performing a surgical procedure on a human skin with a surgical needle, including: determining whether a starting switch which starts the skin resurfacing device is turned on; determining whether a jump start function starting the skin resurfacing device is set by a starting voltage, if an operating voltage of the skin resurfacing device is lower than the starting voltage of the skin resurfacing device at the time of the surgical procedure when the starting switch is turned on; and outputting a jump start voltage to the skin procedure device if it is determined that the jump start function is set.

According to another aspect of the present invention, there is provided a controlling apparatus for a skin resurfacing device performing a surgical procedure on a human skin with a surgical needle, including: a controller; a counter configured to count a driving time of the skin resurfacing device according to a control of the controller; and a starting switch configured to turn on/off a supply of driving power to the skin resurfacing device, wherein the controller controls a timer so as to count only a time when the starting switch is turned on, if the starting switch is turned on and thus a run time mode that is a mode of cumulatively counting only a time when the skin resurfacing device actually performs the skin resurfacing is set.

According to another aspect of the present invention, there is provided a skin resurfacing device for performing a surgical procedure on a human skin with a surgical needle, including: a skin resurfacing unit which includes at least the needle and performs treatment or tattoo; a controller; a counter configured to count a driving time of the skin resurfacing device according to a control of the controller; and a starting switch configured to turn on/off a supply of driving power to the skin resurfacing device, wherein the controller controls a timer so as to count only a time when the starting switch is turned on, if the starting switch is turned on and thus a run time mode that is a mode of cumulatively counting only a time when the skin resurfacing device actually performs the skin resurfacing is set.

According to another aspect of the present invention, there is provided a controlling method for a skin resurfacing device performing a surgical procedure on a human skin with a surgical needle, including: determining whether a run time mode that is a mode of cumulatively counting only a time when a starting switch turning on/off a supply of driving power supplied to the skin resurfacing device is turned on and thus the skin resurfacing device actually performs the skin resurfacing is set; determining whether the starting switch is turned on if it is determined that the run time mode is set; and counting only the time when the starting switch is turned on if the starting switch is turned on.

According to the present invention having the above-described constructions, even when the surgical procedure is performed at the operating voltage of the skin resurfacing unit that is lower than the starting voltage thereof, if the user sets the start function only once simultaneously with setting the operating voltage once, the skin resurfacing unit may automatically perform a jump start function every time it starts to smoothly start the skin resurfacing unit, and after the starting, the skin resurfacing unit may be operated at the operating voltage preset by the user that is the voltage lower than the starting voltage.

Further, the counter (not illustrated) may be controlled so as to selectively count the skin resurfacing time depending on the turn on time of the starting switch, that is, on whether to want to count the working time depending on the run time mode of cumulatively counting only the time when the skin resurfacing unit is actually operated to actually perform the skin resurfacing, or whether to want to count the total time from beginning to end of the skin resurfacing work, including the turn off time of the starting switch frequently occurring during the skin resurfacing work, thereby easily obtaining the total surgical procedure time suitable for the billing system at the time of the skin resurfacing.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a block diagram illustrating a configuration of a skin resurfacing device 100 according to a preferable embodiment of the present invention;

FIG. 2 is a flow chart illustrating an operation of a skin resurfacing device according to Embodiment 1 of the present invention; and FIG. 3 is a flow chart illustrating an operation of a skin resurfacing device according to Embodiment 2 of the present invention.

DETAILED DESCRIPTION OF THE INVENTION

Hereinafter, preferable embodiments of the present invention will be described in detail with reference to the accompanying drawings.

Embodiment 1

First, Embodiment 1 of the present invention will be described. Embodiment 1 relates to a jump start function. Herein, the jump start function means a function of automatically supplying, by a controlling apparatus for a skin resurfacing device, a voltage corresponding to a starting voltage to drive the skin resurfacing device if a user performs the jump start function in a state in which a use voltage in a normal use state of the skin resurfacing device is set, and operating the skin resurfacing device at the use voltage set by the user, which is a first object of the present invention.

FIG. 1 is a block diagram illustrating a configuration of a skin resurfacing device 100 according to a preferable embodiment of the present invention.

As illustrated in FIG. 1, the skin resurfacing device 100 according to Embodiment 1 includes a power supply 10, a controller 20, an input unit 30, a storage unit 40, a voltage regulator 50, a skin resurfacing unit 60, and a display unit 70.

The power supply 10 is a supply source that supplies DC power to the skin resurfacing device 100, but is not limited thereto. Accordingly, in the present embodiment, a DC power supply of 19 V is used.

The voltage regulator 50 regulates the voltage of the DC power supply supplied from the power supply 10 according to a control from the controller 20 and supplies the regulated voltage to the skin resurfacing unit 60.

The skin resurfacing unit 60 includes a motor as a driver for driving the skin resurfacing device, and is used to mean containing of known components including a needle driven by the motor to perform the skin resurfacing. Further, the skin resurfacing device may be a vibration motor when it does not use a general DC motor as a driving force supplying source, but uses a vibration force of other means, for example, the vibration motor, and other means may be used in the present invention.

The controller 20 controls the voltage regulator 50 to perform various controls to be described below simultaneously with turning on or off the supply of power supplied from the power supply 10 to the skin resurfacing unit 60.

The input unit 30 is a means for inputting information required for the user to operate the skin resurfacing device 100 and in the present embodiment, is formed in a touch screen type integrally formed with the display unit 70 to be described below. However, the input unit 30 is not limited to the touch screen type, and other known input means may be used.

The storage unit 40 may store a control program, control data, or the like required to control the skin resurfacing device 100 of the present embodiment.

The display unit 70 is a means visually displaying various types of information associated with an operation state of the skin resurfacing device 100 according to the present embodiment to a user, including the information input from the input unit 30. Therefore, the user may input various types of information required to operate the skin resurfacing device 100 using the input unit 30 while viewing a display content displayed on the display unit 70, and may also check the information on whether the skin resurfacing device 100 is normally operated, or the like by using the display unit 70.

Further, a starting switch 80 such as a foot switch operated by being pressed with a user's foot is provided between the voltage regulator 50 and the skin resurfacing unit 60 of the skin resurfacing device 100. For example, the skin resurfacing device 100 performs the operation controlled by the controller 20 only when the starting switch 80 is turned on using the user's foot, or the like.

In the present disclosure, the skin resurfacing device 100 means an entire device that includes the controller 20, the input unit 30, the storage unit 40, the voltage regulator 50, the skin resurfacing unit 60, the display unit 70, and the starting switch 80. In this case, the power supply 10 may be included or may not be included in the skin resurfacing device 100. Further, a controlling apparatus for the skin resurfacing device 100 means the remaining components except the power supply 10, the starting switch 80, and the skin resurfacing unit 60 among all the components of the skin resurfacing device 100. In this case, the controlling apparatus may include and may not include the voltage regulator 50.

In other words, Embodiment 1 of the present invention may be performed by integrally forming the skin resurfacing unit directly performing the skin resurfacing with the controlling apparatus for controlling the same, by separately forming the skin resurfacing unit from the controlling apparatus, and may be performed by a method for coupling the skin resurfacing unit and the controlling apparatus with each other at the time of the surgical procedure.

Next, an operation of the skin resurfacing device 100 according to Embodiment 1 of the present invention will be described with reference to the accompanying drawings. FIG. 2 is a flow chart illustrating the operation of a skin resurfacing device 100 according to Embodiment 1 of the present invention.

First, when the skin resurfacing device 100 starts, the controller 20 sets the operating voltage for operating the skin resurfacing device 100 in a normal state using the input unit 30, and sets whether to start the skin resurfacing unit 60 by the jump start function, that is, sets whether to perform the jump start function (step S11).

As described above, the controller 20 controls the voltage regulator 50 to start the skin resurfacing unit 60 at the preset jump start voltage (for example, 12V) for a predetermined time after the starting switch 80 is turned on if it is determined that the jump start function is set, and drives the skin resurfacing unit 60 at the operating voltage set by the user if the predetermined time lapses.

Next, the controller 20 checks whether the starting switch 80 is turned on in step S12, repeats step S12 if the starting switch 80 is not turned on, and the process proceeds to step S13 if the starting switch 80 is turned on to allow the controller to check whether the jump start function is set.

If it is determined as the check result in step S13 that the jump start function is set, the controller 20 controls the voltage regulator 50 to output the voltage (in the present embodiment, 12 V) for the jump start to the skin resurfacing unit 60, and the process proceeds to step S15, and then proceeds to step S16 after a predetermined time (in the present embodiment, 200 ms) is delayed. In step S16, the controller 20 controls the voltage regulator 50 to output the operating voltage set by the user in step S11 to the skin resurfacing unit 60, thus to operate the skin resurfacing unit 60 at the operating voltage set by the user.

For example, when the user sets the operating voltage to be 6 V in step S11, the controller 20 allows the voltage regulator 50 to output a voltage of 12 V to the skin resurfacing unit 60 for 200 ms after the starting switch 80 is turned on, thus to smoothly start the skin resurfacing unit 60. Then, the controller 20 allows the voltage regulator 50 to output a voltage of 6 V set by the user in step S11 to the skin resurfacing unit 60 if 200 ms lapses after the starting switch 80 is turned on, thus to operate the skin resurfacing unit 60 at the voltage of 6 V that is the operating voltage set by the user, in other words, to operate the skin resurfacing unit 60 with a speed and a torque corresponding to the voltage of 6 V, thereby performing the skin resurfacing.

As the determination result in step S13, if it is determined that the jump start function is not set, the process jumps to step S16, and thus the controller 20 controls the voltage regulator 50 so as to output the operating voltage set by the user in step S11 to the skin resurfacing unit 60. Therefore, the skin resurfacing unit 60 is driven with the driving voltage set by the user in step S11.

However, when the minimum driving voltage is 10 V at the time of first driving the skin resurfacing unit 60 and the operating voltage set by the user in step S11 is 6 V, the operating voltage set by the user in step S11 is lower than the minimum driving voltage of the skin resurfacing unit 60, thereby causing a problem in which the skin resurfacing unit does not start. Therefore, according to the present embodiment, in step S11, it is configured to set whether the jump start function uses by the user, but it may be configured to perform the jump start function without the process set by the user.

Next, the operation of the skin resurfacing device 100 of FIG. 1 will be described in more detail. Depending on whether the jump start function is set, the controller 20 according to the present embodiment controls the voltage regulator 50 to output the preset jump start voltage to the skin resurfacing unit 60 every time the starting switch 80 is turned on, if it is determined that the jump start function is set, thereby controlling the skin resurfacing unit 60 so as to start at the jump start voltage. If a preset time lapses, the controller 20 controls the voltage regulator 50 to output the operating voltage set by the user to the skin resurfacing unit 60, thereby controlling the skin resurfacing unit 60 to be operated at the operating voltage set by the user.

Therefore, according to the present embodiment, even when the surgical procedure is performed at the operating voltage of the motor of the skin resurfacing unit at the time of the skin resurfacing that is lower than the initial starting voltage of the motor, if the user sets the jump start function only once simultaneously with setting the operating voltage once, the skin resurfacing unit may automatically perform the jump start function every time the motor starts to smoothly start the motor, and after starting the motor, the skin resurfacing unit may be operated at the operating voltage preset by the user that is the voltage lower than the starting voltage.

Embodiment 2

Next, Embodiment 2 of the present invention will be described. A hardware configuration according to Embodiment 2 is basically the same as FIG. 1, and the content and operation of the control performed by the controller are different from those of Embodiment 1.

FIG. 3 is a flow chart illustrating an operation of a skin resurfacing device according to Embodiment 2 of the present invention.

First, in step S21, the user sets an operation mode of the skin resurfacing device 100 as any one of a run time mode and a normal mode. Selecting the operation mode may be performed by the input unit 30 of the skin resurfacing device 100, and the operation mode set by the user is stored in the storage unit 40. Then, the controller 20 operates the skin resurfacing device 100 depending on the operation mode stored in the storage unit 40.

Further, although not illustrated in FIG. 1, the skin resurfacing device 100 may further include a counter for counting an operation time, in which the counter counts the operation time, i.e., the surgical procedure time of the skin resurfacing device 100 depending on a flow to be described below with reference to the flow chart of FIG. 3.

Herein, the run time mode is a mode of cumulatively counting only the time when the skin resurfacing unit 60 of the skin resurfacing device 100 is operated to actually perform the skin resurfacing, and the normal mode is a mode of cumulatively counting a total time from the start time of the surgical procedure to the end time of the surgical procedure using the skin resurfacing device 100, including an idle time when the skin resurfacing unit 60 is not actually operated.

Next, the process proceeds to step S22 to check whether the timer is turned on, and if it is determined that the timer is turned on, proceeds to step S23 to check whether the run time is turned on, that is, whether the skin resurfacing device 100 is set as the run time mode.

Further, as the check result in step S22, if it is determined that the timer is not turned on, the process proceeds to step S24 to turn on the timer and proceeds to step S23.

Next, as the check result in step S23, if it is determined that the run time mode is turned on, the skin resurfacing device 100 is set as the run time mode. Therefore, the process proceeds to step S25 to allow the controller 20 to check whether the starting switch 80 is turned on, and as the check result in step S25, if it is determined that the starting switch 80 is not turned on, continuously, the controller repeatedly checks whether the starting switch 80 is turned on.

Further, as the check result in step S25, if it is determined that the starting switch 80 is turned on, the process proceeds to step S26 to count the time when the starting switch 80 is turned on, and then proceeds to step S28 to check whether the starting switch 80 is turned off.

Further, as the check result in step S28, it is determined that the starting switch 80 is not in the turned off state, in other words, if it is determined that the starting switch 80 is in the turned on state, the process returns to step S26, continuously, the starting switch 80 counts the turned on time. If it is determined that the starting switch 80 is in the turned off state, the process proceeds to step S29 to determine whether the skin surfacing operation using the skin resurfacing device 100 ends.

Further, as the check result in step S29, if it is determined that the skin resurfacing operation ends, the count of the surgical procedure operation time ends, while as the check result in step S29, if it is determined that the skin resurfacing operation does not end, the process returns to step S25 to repeat a routine of the steps S25 to S29.

As the check result in step S23, if the run time mode is not turned on, the skin resurfacing device 100 is set as the normal mode. Therefore, the process proceeds to step S27 to allow the controller 20 to start a count as the normal mode, and then the process proceeds to step S29 to allow the controller to determine whether the skin resurfacing operation using the skin resurfacing device 100 ends.

As described above, according to Embodiment 2 of the present invention, based on the setting of the user, the controller 20 of the skin resurfacing device 100 may control the counter (not illustrated) so as to selectively count the skin resurfacing time depending on whether to want to count the operation time depending on the run time mode of cumulatively counting the turn on time of the starting switch by the user, that is, only the time when the skin resurfacing is actually performed by actually operating the skin resurfacing unit 60, or depending on whether to want to count the total time from beginning to end of the skin resurfacing operation, even including the turn off time of the starting switch 80 frequently generated during the skin resurfacing operation, thereby easily obtaining the total surgical procedure time suitable for the billing scheme at the time of the skin resurfacing.

As described above, the preferable embodiments of the present invention have been described, but is not limited thereto, and therefore may be variously changed or modified within the scope of the present invention.

Further, Embodiments 1 and 2 may be separately performed and a combination thereof may be performed.

What is claimed is:

1. A controlling apparatus for a skin resurfacing device performing a surgical procedure on a human skin with a surgical needle, comprising:

a controller;

a voltage regulator configured to regulate a voltage supplied to the skin resurfacing device from a power supply according to a control of the controller; and a starting switch configured to turn on/off a supply of power between the voltage regulator and the skin resurfacing device, wherein the skin resurfacing device has a preset operating voltage and a preset jump start voltage that is higher than the preset operating voltage, wherein the skin resurfacing device has a jump start mode for starting the skin resurfacing device at the preset jump start voltage, and wherein the controller is adapted to control the voltage regulator so as to output the preset jump start voltage to the skin resurfacing device when the starting switch is turned on during the jump start mode.

2. The controlling apparatus of claim 1, wherein the controller is adapted to control the voltage regulator so as to output the operating voltage to the skin resurfacing device when a predetermined time is delayed after the starting switch is turned on.

3. A skin resurfacing device performing a surgical procedure on a human skin with a surgical needle, comprising:

a skin resurfacing unit which includes at least the needle and performs the surgical procedure;

a controller;

a voltage regulator configured to regulate a voltage supplied to the skin resurfacing unit from a power supply according to a control of the controller; and a starting switch configured to turn on/off a supply of power between the voltage regulator and the skin resurfacing unit, wherein the skin resurfacing device has a preset operating voltage and a preset jump start voltage that is higher than the preset operating voltage, wherein the skin resurfacing device has a jump start mode for starting the skin resurfacing device at the preset jump start voltage, and wherein the controller is adapted to control the voltage regulator so as to output the preset jump start voltage to the skin resurfacing device when the starting switch is turned on during the jump start mode.

4. The skin resurfacing device of claim 3, wherein the controller is adapted to control the voltage regulator so as to output the operating voltage to the skin resurfacing device when a predetermined time is delayed after the starting switch is turned on.

* * * * *